United States Patent [19]

van den Bosch

[11] 4,073,957
[45] Feb. 14, 1978

[54] SPIRO-1,2,4-TRITHIOLAN CONTAINING FLAVORING AGENTS AND METHOD OF USE

[75] Inventor: Steven van den Bosch, Woudenberg, Netherlands

[73] Assignee: P.F.W. Beheer B.V., Amersfoot, Netherlands

[21] Appl. No.: 685,878

[22] Filed: May 12, 1976

[30] Foreign Application Priority Data

July 12, 1975 United Kingdom ............... 29365/75

[51] Int. Cl.² .................. A23L 1/226; A23L 1/231; A23L 1/235; C07D 341/00
[52] U.S. Cl. .................. 426/535; 260/327 R; 260/329 HS; 260/332.3 H
[58] Field of Search ..... 260/327 R, 329 HS, 332.3 H; 426/535

[56] References Cited

U.S. PATENT DOCUMENTS

| B 560,717 | 2/1976 | Wilson et al. | 426/535 |
| 3,958,030 | 5/1976 | Wilson et al. | 426/535 |

FOREIGN PATENT DOCUMENTS 623,330   7/1961   Canada ............... 260/327 R

OTHER PUBLICATIONS

Houben-Weyl, Methoden der Organischem Chemie, vol. 1X (1955) pp. 704, 720 and 721.

Primary Examiner—Richard L. Raymond
Attorney, Agent, or Firm—William S. Alexander

[57] ABSTRACT

New chemical compounds are disclosed having the general formula

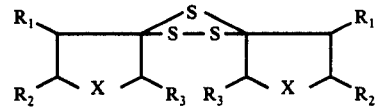

wherein X is oxygen, sulfur, or methylene and $R_1$, $R_2$, and $R_3$ are hydrogen or lower alkyl groups. These compounds are useful in a variety of flavoring applications.

20 Claims, No Drawings

SPIRO-1,2,4-TRITHIOLAN CONTAINING FLAVORING AGENTS AND METHOD OF USE

This invention relates to new sulfur-containing flavouring agents which possess interesting and unexpected organoleptic properties (both olfactory and gustatory) and which are therefore useful in a great variety of flavouring compositions. The invention also comprises flavouring and flavour-enhancing compositions containing the aforedescribed compounds and foodstuffs and food compositions to which such compounds have been added. In recent years, vast increases have been recorded in world population with a corresponding strain on the world's food supply. For a variety of reasons, including the space requirements for raising large herds or flocks of meat producing animals and the quantities of grain required to feed such animals, it has become and will continue to become increasingly expensive and inefficient for man to consume large quantities of meat. From a nutritional standpoint, other materials, such as soya and other vegetable proteins, are the equal of meat protein and a number of food processors have developed meat substitutes and meat extenders based on such materials and meat flavoring additives. These products, however, fall far short of the flavor level required or expected by most consumers.

In response to the stated problem, it is an object of this invention to provide a series of chemical compounds which can be used to impart a meat flavor to non-meat foods or to enhance the meat flavor of such a material either alone or when used in conjunction with other flavoring additives. The compounds of the invention belong to the chemical class of 3,5-dispiro-1,2,4-trithiolans represented by the following structural formula

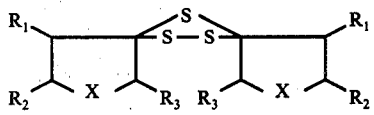

wherein X is selected from the class consisting of oxygen, sulfur, and methylene; and $R_1$, $R_2$, and $R_3$ are selected from the class consisting of hydrogen and alkyl groups having 1 to 3 carbon atoms. It will be understood that most of the compounds of the invention exist in various isomeric forms and the formula given herein represent mixtures of such isomers, as they are recovered from the preparative reaction. The particularly preferred materials according to the present invention for imparting desirable flavour and odour characteristics are those compounds represented by the formula, wherein X has the aforedescribed meaning and $R_1$, $R_2$, and $R_3$ are methyl or hydrogen.

Examplary compounds within the scope of the invention include 3,5-bis(cyclopentyl)spiro-1,2,4-trithiolan
3,5-bis(2'-methylcyclopentyl)spiro-1,2,4-trithiolan
3,5-bis(2'-methyltetrahydrofuryl-3')spiro-1,2,4-trithiolan and
3,5-bis(2'-methyltetrahydrothienyl-3'-spiro-1,2,4-trithiolan.

It has been found that the novel trithiolan derivatives of the present invention possess flavour characteristics remarkably similar to those of prepared meat or meat products and therefore are valuable as food flavouring agents. More particularly, they are useful in enhancing the meat flavour of meat products or meat-containing foods and for imparting a meat flavour to non-meat foods. The flavour application of the compounds, however, are broader than meat. These compounds are also useful components in other foodstuffs such as e.g. dairy flavors and even certain vegetable types such as fruits, maple flavor, or nuts.

It is known that 3,5-dimethyl-1,2,4-trithiolan is a constituent of boiled beef (S.S. Chang et al., Chem. Ind. 1639 (1968)), of roasted filbert volatiles (T. E. Kinlin et al., J. Agr. Food Chem. 20, 1021 (1972)), and of potatoes (R. G. Buttery et al., J. Agr. Food Chem. 18, 538 (1970)). This compound was also isolated and identified from the nonenzymatic browning reaction of the hydrolysed vegetable protein-xylose-cysteine model system (C. J. Mussinan and I. Katz, J. Agr. Food Chem. 21, 43 (1973)). In the chemical literature many examples of 1,2,4-trithiolans are mentioned e.g. dialkyl-, tetraalkyl-, tetrabenzyl-, and tetraphenyl-1,2,4-trithiolans (F. Asinger et al., Ann. 627, 195 (1959); S. B. Tjan et al., Tetrahedron 28, 3489 (1972); E. Campaigne and B. E. Edwards, J. Org. Chem. 27, 4488 (1962); M. M. Campbell and D. M. Evgenios, J. Chem. Soc. 1971, 179). However, 3,5-bis(cyclohexyl)spiro-1,2,4-trithiolan appears to be the only compound described in the chemical literature as an example of 3,5-dispiro-1,2,4-trithiolans (F. Asinger et al., Ann. 627, 195 (1959); F. Asinger et al., (East) German Patent 19.119 of June 9, 1960 (Chem. Abstr. 56, 1459c (1962); F. Asinger et al., German patent 1,079,068 of April 7, 1960 (Chem. Abstr. 55, 17655g (1961)). Asinger et al. teach that 3,5-bis(cyclohexyl)-spiro-1,2,4-trithiolan is suitable as a vulcanization accelerator and for pest control.

The novel compounds of the invention can be prepared according to the method described by F. Asinger et al., Ann. 627, 195 (1959) in which a ketone is reacted with elemental sulfur in the presence of an amine. The starting ketones are commercially available or can be prepared by methods known per se.

It has been found that the compounds of the present invention have characteristic and unexpected organoleptic properties. Even at very low concentration they are useful for enhancing flavours or imparting flavours to materials to which they are added. The same is true both for the meat flavours and the dairy or other flavours for which these compounds have been found to be effective. Flavouring compositions prepared using the compounds of the invention in combination with other flavour-enhancing ingredients can contain about 0.001 to 10% of the novel compounds. When added to a foodstuff the flavouring composition will be used in amounts such that the concentration of the novel compound will be between about 0.01 to 10 ppm based on the weight of the finished foodstuff. Likewise, when the compounds are used alone, they are added in concentrations of about 0.01 to 10 ppm based on the weight of the finished foodstuff.

The term "Flavouring compositions" as used herein means compositions which contribute a part of the overall flavour impression of a foodstuff by supplementing or fortifying its natural or artificial flavour and/or aroma character as well as compositions which supply substantially all of the flavour and/or aroma character to an edible article.

The term "foodstuff" as used herein includes both solid and liquid edible materials for man or animals, which materials usually do, but need not, have nutritional value. Thus, foodstuffs includes meats, gravies, soups, convenience foods, milk and dairy products, nuts, seafoods, including fish, processed foods containing soya and other non-muscle protein, vegetables such as fruits, maple and nuts, cream sauce, dip sauces, salad dressing and the like.

After having established the organoleptic usefulness of the compounds of the present invention, we have prepared and evaluated Asinger's 3,5-bis(cyclohexyl)-spiro-1,2,4-trithiolan. That compound is very weak in odour and was found to be of no value whatsoever in flavouring compositions. We have also prepared and evaluated the novel 3,5-bis(2'-methylcyclohexyl-1')spiro-1,2,4-trithiolan; its properties are comparable with that of the parent compound, in other words also this compound is very weak and uncharacteristic.

The invention is further described by the following examples which are intended to be illustrative only without limiting it in any way. When reference is made to testing by a panel, the panel consisted of five experienced flavorists. The instrumental analytical data used to characterize the inventive compounds were obtained using the following equipment.

1. NMR Spectra were recordd on a JEOL C 60H, 60 MHz instrument, as solutions in $CCl_4$, with tetramethylsilane as internal standard.
2. IR Spectra were measured with a Perkin-Elmer 225 IR spectrophotometer, either neat or as solutions in $CCl_4$.
3. Mass Spectra were determined on an AEI MS30/DS50 double-focusing (Nier-Johnson) mass spectrometer/data system, at 70 EV, source temperature 200° C. The 10 strongest peaks are given, the first one being the base peak (100%).

EXAMPLE 1

Preparation of
3,5-bis(2'-methylcyclopentyl)spiro-1,2,4-trithiolan
($R_1$=H, $R_2$=H, $R_3$=$CH_3$, X=$CH_2$)

In a three-necked 250 ml round-bottomed flask provided with a mechanical stirrer, thermometer, gas inlet tube and gas outlet tube are placed 39,0 g (= 0,410 mole) of 2-methylcyclopentanone (prepared according to the procedure described by R. Mayer, Neuere Methoden der praparativen organischen Chem. Bd. II, 69 (1960)) and 30.0 g (= 0.425 mole) of n-butylamine. The stirrer is started and the flask is cooled to 0° C. At that temperature the reaction mixture is saturated with hydrogen sulfide and subsequently 6.4 g (= 0.200 mole) of sulfur is added in small portions. After the sulfur is dissolved, the reaction mixture is allowed to reach room temperature and at that temperature a slow stream of hydrogen sulfide is passed into the solution for an additional 12 hours. After that, 60 ml of an aqueous 50% solution of acetic acid is added dropwise to decompose the aminhydrogensulfide. The reaction mixture is extracted twice with 100 ml of ether. The extracts are washed with water and dried over anhydrous sodium sulfate. Distillation gives the title compound (23 g) as a mixture of isomers; bp. 120°–122° C/2 mm Hg, $n_D^{20}$ 1,5729.

Spectral data of the compound as a mixture of isomers:

| NMR spectrum ($\delta$ in ppm) | IR spectrum |
| --- | --- |
| $\delta$ = 1,13 (d, 3H) | 2955, 2925(sh), 2865, 1446, 1373, |
| $\delta$ = 1,16 (d, 3H) | 1332, 1295, 1290, 1220, 1184, 1118, |
| $\delta$ = 1,83 (m, 6H) | 1090, 1050, 1013, 931, 873 cm$^{-1}$. |
| $\delta$ = 2,33 (m, 8H) | |
| MS spectrum (m/e) | |
| 81, 114, 115, 79, 41, 67, 70, 55, 39. | |

EXAMPLE 2

Preparation of
3,5-bis(2'-methyltetrahydrofuryl-3')spiro-1,2,4-trithiolan ($R_1$=H, $R_2$=H, $R_3$=$CH_3$, X=O)

This compound was prepared according to the procedure described in Example 1, by reacting a mixture of 2-methyltetrahydrofuranone-3 (prepared by the procedure described by M. A. Gianturco et al., Tetrahedron 20, 1763 (1964)) and n-butylamine with hydrogen sulfide and sulfur (bp. 137°–141° C/2 mm Hg; $n_D^{20}$ 1,5615). Spectral data of the title compound as a mixture of isomers after purification by liquid chromatography:

| NMR spectrum ($\delta$ in ppm) | IR spectrum |
| --- | --- |
| $\delta$ = 1,3 (d, 3H) | 2970, 2925, 2875, 2680, 1475, 1440, |
| $\delta$ = 1,36(d, 3H) | 1376, 1358, 1309, 1270, 1150, 1117, |
| $\delta$ = 2,6 (m, 4H) | 1086, 1050, 1033, 1011, 910, 858, |
| $\delta$ = 3,9 (m, 6H) | 600, 435 cm$^{-1}$. |
| MS spectrum (m/e) | |
| 43, 84, 116, 83, 71, 76, 39, 148, 45, 115. | |

EXAMPLE 3

Preparation of
3,5-bis(2'-methyltetrahydrothienyl-3')spiro-1,2,4-trithiolan ($R_1$=H, $R_2$=H, $R_3$=$CH_3$, X=S)

This compound was prepared according to the procedure described in Example 1, by reacting a mixture of 2-methyltetrahydrothiophenone-3 (prepared by the procedure described by P. Karrer and H. Schmid, Helv. Chim. Acta 27, 124 (1944)) and n-butylamine with hydrogensulfide and sulfur ($n_D^{20}$ 1,6475).

Spectral data of the title compound as a mixture of isomers after purification by liquid chromatography:

| NMR spectrum ($\delta$ in ppm) | IR spectrum |
| --- | --- |
| $\delta$ = 1,45   (d, 6H) | 2960, 2920, 2860, 1445, 1430, 1372, |
| $\delta$ = 2,0    (m, 4H) | 1320, 1294, 1262, 1214, 1185, 1146, |
| $\delta$ = 2,7–3,2(m, 6H) | 1116, 1078, 1023, 986, 958, 906, 822, |
| | 798, 780, 685, 625 cm$^{-1}$. |
| MS spectrum (m/e) | |
| 100, 132, 99, 131, 59, 85, 45, 71, 163, 296. | |

EXAMPLE 4

Preparation of 3,5-bis(cyclopentyl)spiro-1,2,4-trithiolan
($R_1$=H, $R_2$=H, $R_3$=H, X=$CH_2$)

This compound was prepared according to the procedure described in Example 1, by reacting a mixture of cyclopentanone (commercial sample) and n-butylamine with hydrogen sulfide and sulfur (mp. 77.2°–78.8° C (microscope heating stage method)).

Spectral data of the title compound:

| NMR spectrum ($\delta$ in ppm) | IR spectrum (in $CCl_4$) |
| --- | --- |
| $\delta$ = 1,9 (m, 8H) | 2960, 2870, 1468(sh), 1449, 1439, |
| $\delta$ = 2,3 (m, 8H) | 1302, 1180, 1050, 1030, 945, 888 cm$^{-1}$. |

| NMR spectrum (δ in ppm) | IR spectrum (in CCl₄) |
|---|---|

MS spectrum (m/e)
67, 100, 70, 41, 101, 99, 133, 76, 58, 65.

EXAMPLE 5

3,5-bis(2'-Methyltetrahydrofuryl-3')spiro-1,2,4-trithiolan was added to a clear commercially available beef broth at a level of 0.5 ppm. The beef broth thus obtained was panel tested against a sample of the same broth without the abovementioned trithiolan. The panel was unanimous in its preference for the broth containing the compound of the invention, since this beef broth showed a very good improvement of the beefy taste.

EXAMPLE 6

3,5-bis(2'-Methylcyclopentyl)spiro-1,2,4-trithiolan was added to a clear commercially available beef broth at a level of 0.1 ppm. The beef broth thus obtained was panel tested against a sample of the same broth not containing the above-mentioned trithiolan. It was found that the broth containing the compound of the invention possessed an increased creamy, meaty taste.

EXAMPLE 7

A gravy was prepared by mixing the following ingredients:

| Ingredients: | grams |
|---|---|
| whey powder | 12,5 |
| fat flakes (edible) | 20 |
| sodium chloride | 17,5 |
| monosodium glutamate | 5 |
| hydrolysed vegetable protein | 7,5 |
| corn starch | 30 |
| caramel powder | 5,25 |
| onion flakes (freeze dried) | 0,25 |
| locust bean gum | 2 |

40 Grams of this mixture were dissolved in 960 grams of boiling water to obtain 1 kg of the gravy. The gravy was well stirred and simmered for 5 minutes. The gravy was divided into three portions.

To one portion of the gravy 3,5-bis(2'-methyltetrahydrofuryl-3')spiro-1,2,4-trithiolan was added at a level of 0.5 ppm. The obtained gravy was panel tested against the control, which was the gravy without the compound of the invention. The panel showed a clear preference for the gravy with the above-mentioned trithiolan, since it had a good roast meaty taste, which was absent in the gravy not containing the compound of the invention.

To a second portion of the gravy 3,5-bis(2'-methylcyclopentyl)spiro-1,2,4-trithiolan was added at a level of 0.1 ppm. The obtained gravy was tested against the control. The gravy with the said compound was found to possess a good overall meaty taste, which was absent in the gravy without the compound of the invention.

EXAMPLE 8

A butter flavour was prepared by mixing the following ingredients:

| Ingredients | grams |
|---|---|
| acetoin | 100 |
| trans-2-hexenal | 5 |
| dimethylsulfide (1% solution | 6 |
| in propylene glycol) | |
| butyric acid | 10 |
| diacetyl | 7 |
| propylene glycol | 100 |
| glycerine | 772 |

The resulting mixture was divided into two portions of 500 g. To one portion of the butter flavour 0.5 g of 3,5-bis(cyclopentyl)spiro-1,2,4-trithiolan was added. Both butter flavours were tested in commercially available instant mashed potatoes. To 1 kg of the mashed potatoes 0.1 g of the flavour was added. The level of 3,5-bis(cyclopentyl)spiro-1,2,4-trithiolan in the mashed potatoes can be expressed as 0.1 ppm. The butter flavour with the compound of the invention was unanimously preferred by the test panel over the butter flavour not containing the compound, since it possessed a more pronounced buttery, creamy taste.

What is claimed is:

1. A chemical compound having the structural formula

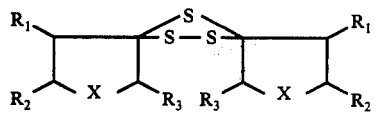

wherein X is selected from the class consisting of O, S, and —CH₂—, and $R_1$, $R_2$, and $R_3$ are hydrogen or alkyl groups having 1 to 3 carbon atoms.

2. 3,5-bis(cyclopentyl)spiro-1,2,4-trithiolan 3. 3,5-bis(2'-methylcyclopentyl)spiro-1,2,4-trithiolan 4. 3,5-bis(2'-methyltetrahydrofuryl-3')spiro-1,2,4-trithiolan 5. 3,5-bis(2'-methyltetrahydrothienyl-3')spiro-1,2,4-trithiolan 6. A food stuff to which has been added a chemical compound having the structural formula

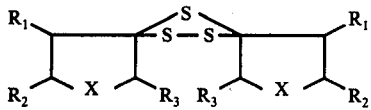

wherein X is selected from the class consisting of O, S, and —CH₂—, and $R_1$, $R_2$, and $R_3$ are hydrogen or alkyl groups having 1 to 3 carbon atoms, said compound being added in an amount sufficient to alter the flavor thereof.

7. The foodstuff of claim 6 where the compound is 3,5-bis(cyclopentyl)spiro-1,2,4-trithiolan 8. The foodstuff of claim 6 where the compound is 3,5-bis(2'-methylcyclopentyl)spiro-1,2,4-trithiolan.

9. The foodstuff of claim 6 wherein the compound is 3,5-bis(2'-methyltetrahydrofuryl-3')spiro-1,2,4-trithiolan.

10. The foodstuff of claim 6 wherein the the compound is 3,5-bis(2'-methyltetrahydrothienyl-3')spiro-1,2,4-trithiolan.

11. A flavoring composition containing, in combination with other flavor enhancing ingredients, a chemical compound having the structural formula

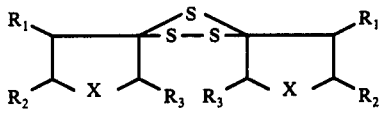

wherein X is selected from the class consisting of O, S, and —CH$_2$—, and R$_1$, R$_2$ and R$_3$ are H, or an alkyl radical having 1 to 3 carbon atoms.

12. A composition according to claim 11 wherein the compound is 3,5-bis(cyclopentyl)spiro-1,2,4-trithiolan.

13. A composition according to claim 11 wherein the compound is 3,5-bis(2'-methylcyclopentyl)spiro-1,2,4-trithiolan.

14. A composition according to claim 11 wherein the compound is 3,5-bis(2'-methyltetrahydrofuryl-3')spiro-1,2,4-trithiolan.

15. A composition according to claim 11 wherein the compound is 3,5-bis(2'-methyltetrahydrothienyl-3')spiro-1,2,4-trithiolan.

16. A method of imparting flavor to or enhancing the flavor of a foodstuff which comprises incorporating therein an effective amount of a chemical compound having the formula

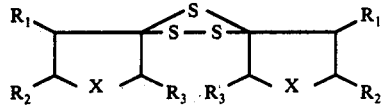

wherein X is selected from the class consisting of O, S, and —CH$_2$—, and R$_1$, R$_2$, and R$_3$ are hydrogen or an alkyl radical having 1 to 3 carbon atoms.

17. The method of claim 16 wherein the compound is 3,5-bis(cyclopentyl)spiro-1,2,4-trithiolan.

18. The method of claim 16 wherein the compound is 3,5-bis(2'-methylcyclopentyl)spiro-1,2,4-trithiolan.

19. The method of claim 16 wherein the compound is 3,5-bis(2'-methyltetrahydrofuryl-3')spiro-1,2,4-trithiolan.

20. The method of claim 16 wherein the compound is 3,5-bis(2'-methyltetrahydrothienyl-3')spiro-1,2,4-trithiolan.

* * * * *